United States Patent [19]

Fischer

[11] Patent Number: 4,997,371

[45] Date of Patent: Mar. 5, 1991

[54] DENTAL AGENT APPLICATOR

[75] Inventor: Dan E. Fischer, Sandy, Utah

[73] Assignee: Honda Giken Kogyo Kabushiki Kaisha, Tokyo, Japan

[21] Appl. No.: 210,390

[22] Filed: Jun. 22, 1988

[51] Int. Cl.⁵ .............................................. A61C 5/04
[52] U.S. Cl. ..................... 433/90; 604/310; 604/311
[58] Field of Search ............... 433/89, 90; 604/3, 4, 604/184, 222, 2, 310, 311; 132/75, 74.5, 73; 401/129

[56] References Cited

U.S. PATENT DOCUMENTS

| | | |
|---|---|---|
| 374,026 | 11/1887 | Williams . |
| 392,006 | 10/1888 | Carmichael . |
| 762,603 | 6/1904 | Witkowski . |
| 833,044 | 10/1906 | Goodhugh . |
| 860,555 | 7/1907 | Middaugh . |
| 870,573 | 11/1907 | Myers . |
| 977,825 | 12/1910 | Murphy . |
| 1,115,561 | 11/1914 | Northey . |
| 1,164,430 | 12/1915 | Thurman . |
| 1,245,153 | 11/1917 | Evslin . |
| 1,438,064 | 12/1922 | Simmons . |
| 1,573,224 | 2/1926 | Condit .............. 604/310 |
| 1,711,352 | 4/1929 | Jeffreys . |
| 1,711,516 | 5/1929 | Alland . |
| 1,908,403 | 5/1933 | Budde . |
| 2,090,354 | 8/1937 | Massman .............. 128/269 |
| 2,100,157 | 11/1937 | Chandler .............. 128/269 |
| 2,104,651 | 1/1938 | Hoffman .............. 132/74.5 |
| 2,170,222 | 8/1939 | Strauss .............. 128/269 |
| 2,643,655 | 6/1953 | McKay .............. 128/220 |
| 2,754,590 | 7/1956 | Cohen . |
| 2,902,035 | 9/1959 | Hartley .............. 128/234 |
| 3,175,242 | 3/1965 | Kamondy et al. .............. 15/559 |
| 3,234,918 | 2/1966 | Gigli .............. 120/45.4 |
| 3,270,743 | 9/1966 | Gingras .............. 128/215 |
| 3,337,095 | 8/1967 | Marbach et al. .............. 222/309 |
| 3,346,147 | 10/1967 | Higgins et al. .............. 222/326 |
| 3,369,543 | 2/1968 | Ronco .............. 128/269 |
| 3,434,209 | 3/1969 | Weissman .............. 33/85 |
| 3,462,840 | 8/1969 | Ellman .............. 32/60 |
| 3,512,526 | 5/1970 | Fielding .............. 128/239 |
| 3,519,364 | 7/1970 | Truhan .............. 401/177 |
| 3,572,337 | 3/1971 | Schunk .............. 128/222 |
| 3,581,399 | 6/1971 | Dragan .............. 32/60 |
| 3,587,575 | 6/1971 | Lichtenstein .............. 128/215 |
| 3,759,259 | 9/1973 | Truhan .............. 128/269 |

(List continued on next page.)

OTHER PUBLICATIONS

Advertisement for Dento-Infusor and Astringedent (1982).

Tissue Management for making Impressions, Dan E. Fischer, reprinted from Restorative Techniques for Individual Teeth (Masson Monographs in Dentistry, vol. 2), Masson Publishing U.S.A., Inc., Chapter 15, pp. 247-265.

Clinical Research Associates Newsletter, vol. 3, Issue 8, Aug., 1979.

Hemostasis During Crown and Bridge Impression Procedures—A New Technique, Barry G. Dale, D.M.D.

Primary Examiner—Cary E. Stone
Attorney, Agent, or Firm—Lyon & Lyon

[57] ABSTRACT

An apparatus for applying dental bonding agents to tooth surfaces. The apparatus includes a syringe-type dispenser for holding a quantity of bonding agent and an applicator tip having short bristles at one end. The applicator tip is curved to accommodate access to tooth surfaces undergoing restorative dental procedures. The short bristles are in communication with the syringe-type dispenser, thereby allowing the bonding agent to be continuously applied to the tooth surfaces without the need to stop the procedure and rewet the applicator in a bonding agent source. The syringe-type applicator permits accurate control over the amount of bonding agent applied to the tooth surface. In this way, the tooth surface receives neither an excessive nor an insufficient amount of the bonding agent. Moreover, the short bristles permit the bonding agent to be applied to the tooth surface without damaging the fragile crystalline structure produced during acid etching.

30 Claims, 1 Drawing Sheet

U.S. PATENT DOCUMENTS

| | | | |
|---|---|---|---|
| 3,760,503 | 9/1973 | Baskas | 32/17 |
| 3,792,699 | 2/1974 | Tobin et al. | 128/2 W |
| 3,894,538 | 7/1975 | Richter | 128/260 |
| 3,896,552 | 7/1975 | Russell | 32/34 |
| 3,910,706 | 10/1975 | Del Bon | 401/134 |
| 3,918,435 | 11/1975 | Beall et al. | 128/2 W |
| 3,924,623 | 12/1975 | Avery | 128/269 |
| 3,938,898 | 2/1976 | Reitknecht | 401/183 |
| 4,030,496 | 6/1977 | Stait et al. | 128/215 |
| 4,143,428 | 3/1979 | Cohen | 3/36 |
| 4,157,709 | 6/1979 | Schuster et al. | 128/759 |
| 4,225,254 | 9/1980 | Holberg | 401/119 |
| 4,243,035 | 1/1981 | Barrett | 128/215 |
| 4,318,403 | 3/1982 | Sneider | 128/232 |
| 4,329,990 | 5/1982 | Sneider | 128/239 |
| 4,522,593 | 6/1985 | Fischer | 433/136 |
| 4,551,100 | 11/1985 | Fischer | 433/218 |
| 4,578,050 | 3/1986 | Fischer | 604/2 |
| 4,813,871 | 3/1989 | Friedman | 433/90 |

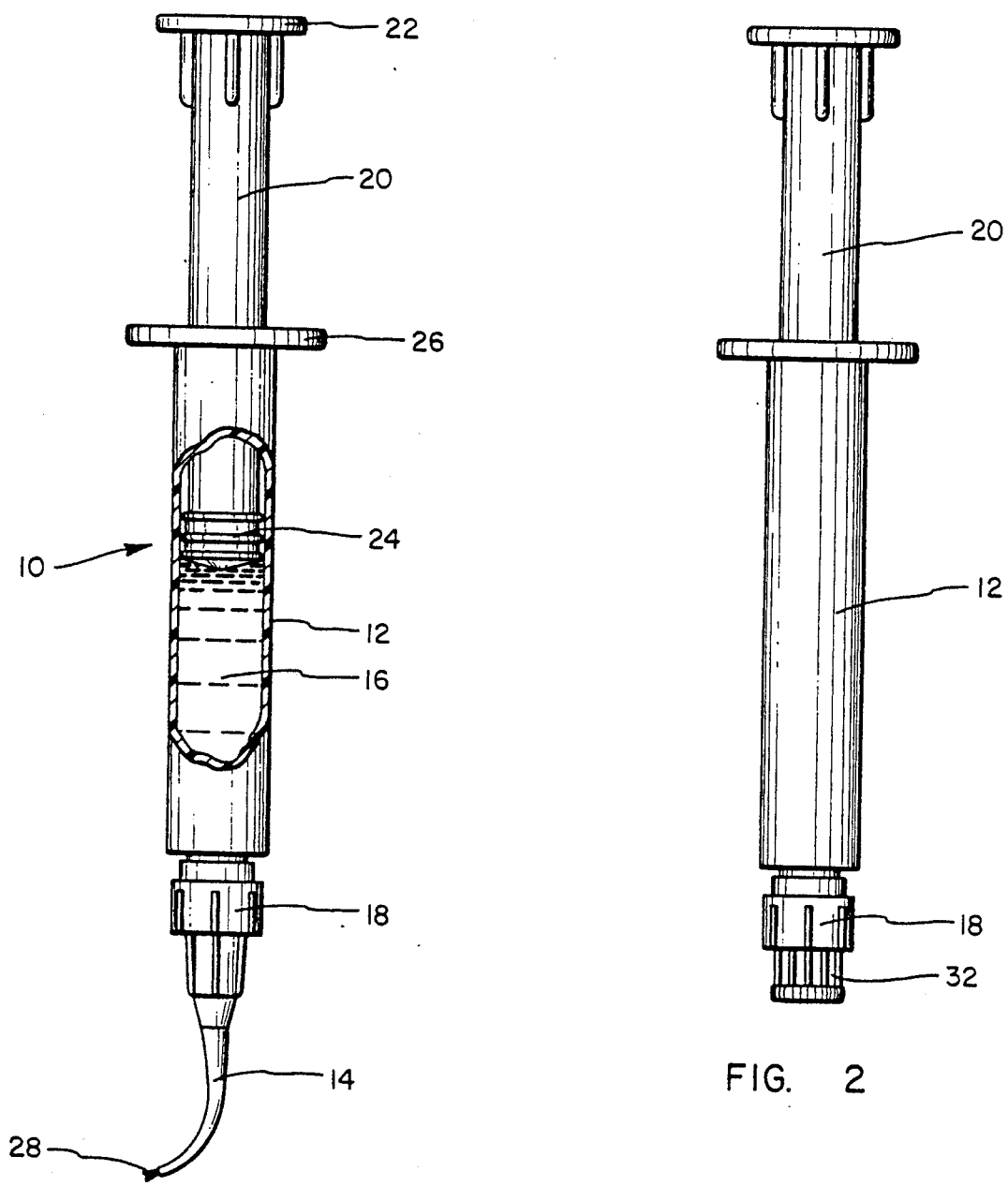
FIG. 1
FIG. 2
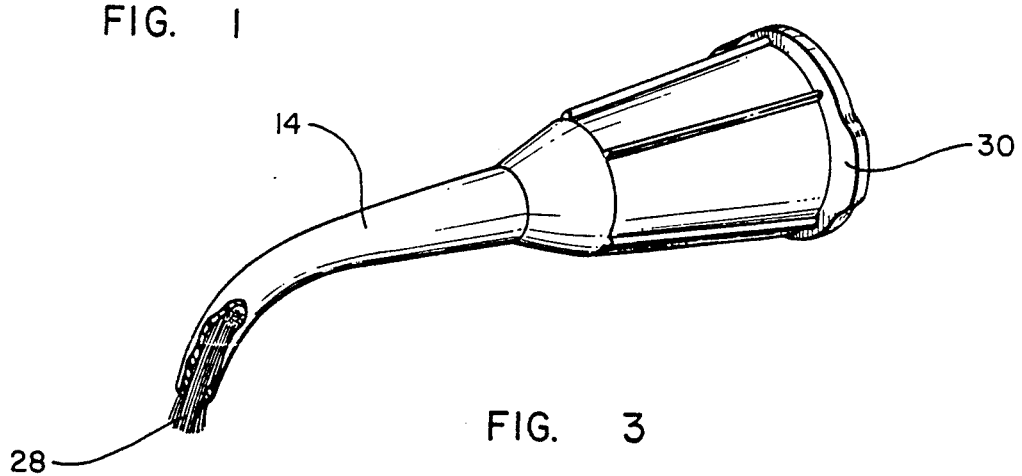
FIG. 3

DENTAL AGENT APPLICATOR

BACKGROUND

1. The Field of the Invention

The present invention relates to apparatus for applying dental agents to tooth surfaces. More particularly, the present invention allows a dentist to quickly and precisely apply a proper quantity of dental agent to tooth surfaces which have been prepared to receive the dental agent. The present invention is ideally suited for applying dental bonding agents to tooth surfaces.

2. The Prior Art

Bonding agents play an important role in dental restorative techniques. Generally, bonding agents are applied to tooth surfaces in order to firmly attach a restoration to the tooth. When the restoration is a composite resin restoration, the composition of the bonding agent is usually that of the matrix of the composite resin.

Before applying a bonding agent, the enamel around a cavity preparation is etched with acid. Acid etching of enamel creates micro-irregularities on the enamel surface. The resin in the bonding agent is usually diluted with monomers so that it has a low viscosity which can readily penetrate into the microscopic irregularities and undercuts produced by the acid etching. The bonding agent is then polymerized. It is believed that when the composite restorative resin is inserted into the cavity, it will polymerize to the bonding agent present on the cavity surface. In this way, better adaptation to the enamel walls of the cavity is achieved with improved mechanical retention of the restoration.

Various devices have been used in the art for applying dental bonding agents to tooth surfaces. One device used to apply dental bonding agents is a small porous sponge or swabbing material. In practice, a quantity of bonding agent is applied to a transfer pad. A sponge is then grasped with forceps and dipped into the bonding agent. The wetted sponge is then rubbed across the tooth surface in order to apply the bonding agent.

The small sponges are disposable to prevent cross-contamination. However, the sponges do not permit accurate application of the bonding agent. Frequently, the bonding agent is applied to surrounding surfaces which do not need treatment. Moreover, the rubbing action required to apply the bonding agent necessarily damages the fragile crystalline surface structure of the tooth formed during acid etching. Once the crystalline surface structure of the tooth is damaged, its bondability is reduced.

Another existing device for applying bonding agent to tooth surfaces is a small disposable brush tip. Like the sponge, the brush tip must be held with forceps or some other holding device. The brush tip is then dipped into a quantity of bonding agent placed on a transfer pad.

Like the sponge, the brush tip is disposable. In addition, the brush tip does not damage the fragile crystalline structure of the tooth surface produced by acid etching. However, like the sponge, the brush tip must constantly be rewetted by the bonding agent during the dental procedure. Moreover, the disposable brush tips used in the art usually have long bristles which do not form a fine tip. As a result, the bonding agent is often inadvertently applied to surrounding tooth surfaces.

Yet another device for applying bonding agents to tooth surfaces is a very fine paint brush. Such a brush can apply the bonding agent to tooth surfaces with precision and detail.

Despite its advantages, a paint brush must also be repeatedly dipped into a quantity of bonding agent during the procedure. In addition, a paint brush is difficult to properly sterilize and is usually nondisposable, thereby making it difficult for the dentist to maintain an aseptic environment. With the ever-increasing threat of Acquired Immune Deficiency Syndrome ("AIDS") in society, use of a nondisposable applicator which is also difficult to sterilize has become unacceptable.

Further, in each of the known devices for applying bonding agents to tooth surfaces, a quantity of bonding agent is placed on a transfer pad so that the device can be rewetted during the surgical procedure. Such a technique is not only wasteful, but is exposes the bonding agent to light, air, and airborne contaminants.

Moreover, time is often of the essence in applying bonding agents to tooth surfaces. As a result, it is important for bonding agents to be applied quickly and accurately. Thus, the need to constantly rewet the bonding agent applicator during the procedure is not only inefficient, but may reduce the effectiveness of the resulting bond between the restoration and the tooth surface.

BRIEF SUMMARY AND OBJECTS OF THE INVENTION

The present invention seeks to resolve a number of the problems which have been experienced in the art, as identified above. More importantly, the apparatus of this invention constitutes an important advancement in the art of dental bonding agent applicators, as evidenced by the following objects and advantages realized by the invention over the prior art.

One object of the present invention is to provide apparatus and methods of applying bonding agents to tooth surfaces which permit continuous application of the bonding agent without the need to stop the dental procedure and rewet the applicator in a bonding agent source.

Another important object of the present invention is to provide apparatus and methods of applying bonding agents to tooth surfaces which permit accurate application of the bonding agent to the precise tooth area that needs treatment.

An additional important object of the present invention is to provide an apparatus for applying bonding agents to tooth surfaces which may be disinfected and which is disposable, thereby enabling the dentist to maintain an aseptic environment.

Still another object of the present invention is to provide apparatus and methods of applying bonding agents to tooth surfaces which permit the bonding agent to be applied directly to the teeth from a sterile source not exposed to air, light, and airborne contaminants.

A further important object of the present invention is to provide apparatus and methods of applying bonding agents to tooth surfaces which does not require the use of a transfer pad.

Yet another important object of the present invention is to provide apparatus and methods of applying bonding agents to tooth surfaces which give the dentist greater control over the flow of bonding agent to the tooth surface.

Additional objects and advantages of the invention will be apparent from the description which follows, or may be learned by the practice of the invention.

The present invention is directed to an apparatus for applying dental bonding agents to tooth surfaces. The apparatus includes a syringe-type dispenser for holding a quantity of bonding agent and a removable applicator tip having short bristles at one end. The applicator tip is curved to accommodate access to tooth surfaces undergoing restorative dental procedures. The short bristles are in communication with the syringe-type dispenser, thereby allowing the bonding agent to be continuously applied to the tooth surfaces without the need to stop the dental procedure and rewet the applicator in a bonding agent source.

The bonding agent remains in a sterile receptacle until applied directly to the tooth surface. In this way, the bonding agent is not exposed to light, air, and airborne contaminants. In addition, there is no need for a transfer pad.

The syringe-type applicator permits accurate control over the amount of bonding agent applied to the tooth surface. Thus, the tooth surface receives neither an excessive nor an insufficient amount of the bonding agent. Moreover, the short bristles permit the bonding agent to be applied to the tooth surface without damaging the fragile crystalline structure produced during acid etching.

BRIEF DESCRIPTION OF THE DRAWINGS

In order to more fully understand the manner in which the above-recited advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the presently preferred embodiments and the presently understood best mode of the invention will be described with additional detail through use of the accompanying drawings in which:

FIG. 1 is a plan view of one presently preferred embodiment within the scope of the present invention with a cut-away portion illustrating the plunger assembly within the syringe barrel;

FIG. 2 is a plan view of the syringe barrel and plunger portion of the embodiment illustrated in FIG. 1 with the applicator tip being replaced with a cap; and FIG. 3 is an enlarged perspective view of the applicator tip element of the present invention with a cut-away portion illustrating the brush tip feature of the present invention.

DETAILED DESCRIPTION OF THE PREFERRED EMBODIMENTS

Reference is now made to the drawings wherein like parts are designated with like numerals throughout. Referring first to FIG. 1, one presently preferred embodiment of the apparatus of the present invention is illustrated and generally designated 10.

Dental bonding agent applicator 10 includes a syringe barrel 12 and applicator tip 14. Syringe barrel 12 is generally cylindrical in shape and is adapted for holding a quantity of dental bonding agent 16.

In the embodiment of the present invention illustrated in FIG. 1, applicator tip 14 is removable. Affixed to the lower end of syringe barrel 12 is a female luer-lock coupling 18. Removable applicator tip 14 is secured to syringe barrel 12 through coupling 18. Other means may be used to couple the applicator tip to the syringe barrel. For example, a screw fit or press-fit coupling mechanism is suitable.

In another embodiment within the scope of the present invention, applicator tip 14 is permanently secured to the syringe barrel. The applicator tip may be integrally molded as part of the syringe barrel or it may snap on irreversibly to the syringe barrel. In such an embodiment, the syringe barrel could be configured to hold only a sufficient quantity of dental bonding agent for a single application. Thereafter, the device would be discarded.

Longitudinally slidable within syringe barrel 12 is plunger 20. Plunger 20 has at its proximal end a thumb disk 22 and at its distal end a plunger head 24. Plunger head 24 is constructed out of a resilient material such that its outer edge is contiguous with the inner wall of the syringe barrel 12. In addition, plunger head 24 is preferably constructed of a material which is non-reactive with dental bonding agent 16.

At the proximal end of syringe barrel 12 are a pair of finger wings 26. Although conventional syringes function by placing two fingers on the finger wings 26 and depressing thumb disk 22 with the thumb, the present invention is preferably used by placing the fingers and thumb around syringe barrel 12 and depressing thumb disk 22 by the palm of the hand. This unique method of use gives the dentist greater control in applying the dental bonding agent. Plunger 20 longitudinally enters syringe barrel 12. As a result, plunger head 24 presses against bonding agent 16 causing the bonding agent to flow out of syringe barrel 12 and through the removable applicator tip 14.

At the distal end of the removable applicator tip are a plurality of bristles 28 which form a brush. The bristles are preferably constructed of soft fibers which allow the bonding agent to be applied to the tooth surfaces without damaging the fragile crystalline structure formed by acid etching the surface. Soft nylon is one suitable material for constructing the bristles.

As shown in FIG. 3, the bristles 28 are tightly packed in the distal end of the applicator tip 14. The bristles are preferably held in place due to friction among the bristles and with the inner wall of applicator tip 14. How tight bristles 28 fit within applicator tip 14 is a function of the bristle count and bristle diameter. The larger the bristle diameter, the fewer bristles will fit within applicator tip 14. The bristles should be packed just tight enough to allow dental bonding agent to flow between the bristles, but not so loosely that the bristles flow out applicator tip 14 along with the bonding agent.

Bristle size affects the flow of bonding agent 16 between packed bristles. If the bristles have a large diameter, then voids exist between packed bristles through which the bonding agent can flow. On the other hand, if the bristles have a small diameter, then very small voids exist between the packed bristles significantly limiting the available space through which the bonding agent can flow. Thus, the larger the bristles, the easier it is to flow bonding agent between packed bristles. In one currently preferred embodiment within the scope of the present invention, the bristle diameter is in the range from about 0.002 inches to about 0.005 inches, and preferably in the range from about 0.0025 inches to about 0.003 inches.

In another embodiment within the scope of the present invention, bristles 28 are held in place by slightly crimping applicator tip 14. In order to crimp the applicator tip, it is preferably constructed of a crimpable material, such as metal.

The bristles extend beyond the distal end of applicator tip 14 a distance in the range from about 1/16 inch to about 5/16 inch. The bristles extend within applicator tip 14 a distance sufficient to engage the inner wall of the applicator tip and hold them in place. In one preferred embodiment within the scope of the present invention, the bristles extend a distance in the range from about ¼ inch to about ½ inch within the applicator tip.

The bristles form a small point at the distal end, thereby permitting accurate application of the bonding agent to the tooth surface. In this way, the exact quantity of bonding agent may be applied to the precise tooth surface that needs treatment and not to surrounding surfaces. The removable applicator tip is curved to facilitate application of the bonding agent to hard-to-reach tooth surfaces.

In one embodiment of the present invention, the distance bristles 28 which extend beyond the distal end of applicator tip 14 may be manually adjusted by the dentist by either pushing the bristles further in or pulling them further out. Adjusting the length of the bristles gives the dentist even greater control in applying the dental bonding agent. By pushing the bristles further within applicator tip 14, the dentist has more pinpoint control in applying the bonding agent. By pulling the bristles further out from the applicator tip, the dentist can cause the bristles to fan out and accurately coat a larger tooth surface.

In addition, FIG. 3 illustrates a male luer-lock fitting 30 on the applicator tip. The male luer-lock fitting is designed to engage female luer-lock coupling 18. Should coupling 18 be constructed in a press-fit or screw-fit embodiment, then fitting 30 should be a corresponding press-fit or screw-fit embodiment so that the applicator tip may be removably attached to syringe barrel 12.

As illustrated in FIG. 2, the applicator tip may be removed and replaced with a cap 32. In one embodiment of the invention, the syringe barrel may be marketed pre-filled with bonding agent and capped with cap 32. Alternatively, the syringe barrel 12 may be filled with bonding agent by removing cap 32 and drawing the desired amount into the barrel.

In use, cap 32 is removed and replaced with applicator tip 14. After the bonding agent is applied to the tooth surface, the applicator tip is removed and discarded. Cap 32 is then replaced, and the syringe barrel is stored until bonding agent is needed in the future. If used properly, the syringe barrel should still be clean; nevertheless, the syringe barrel may be disinfected, if necessary.

Bonding agent applicator 10 is constructed of easy to disinfect materials. The syringe barrel, plunger, coupling, and applicator tip are preferably constructed of rigid plastic, though other suitable construction materials such as glass or metal may be used. It is also important that the syringe barrel, plunger, coupling, and applicator tip be constructed of a material which will not react with dental bonding agent 16. In addition, the bonding agent should not adhere to the construction material.

Because bonding agents are often light sensitive, the bonding agent applicator is generally constructed of an opaque material. Thus, the syringe barrel, applicator tip, plunger, and coupling are preferably constructed of black plastic. Different colored plastic may be used to identify the type of bonding agent within the syringe barrel. Alternatively, printing or other identifying markings on the syringe barrel may be used to identify the type of bonding agent. In addition, markings on the outer surface of the syringe barrel or plunger may be used to identify the volume of bonding agent used or remaining.

The plunger within the syringe barrel permits controlled dispensing of the bonding agent to the tooth surface. It will be appreciated that other means may be used to control the dispensing of the bonding agent. For example, the bonding agent applicator may be adapted for capsule use or for squeeze-bulb use.

Although the above discussion has described an apparatus for applying dental bonding agents to tooth surfaces, it will be appreciated that the apparatus may be adapted for applying other dental agents to tooth surfaces. Other dental agents, such as dentin sealants, for example, need to be precisely applied to specific tooth surfaces in a very thin layer. Suitable dental agents should preferably have a viscosity low enough to flow through the small spaces between bristles 28, but not so low that the dental agent runs freely out the apparatus. In such cases, the apparatus within the scope of the present invention may be advantageously used to apply other dental agents. Thus, the foregoing discussion regarding bonding agents is equally applicable to other similar dental agents.

From the foregoing, it will be appreciated that the present invention provides apparatus and methods for applying bonding agents to tooth surfaces which permit continuous application of the bonding agent without the need to stop the dental procedure and rewet the applicator in a bonding agent source.

Additionally, it will be appreciated that the present invention further provides apparatus and methods for applying bonding agents to tooth surfaces which permit accurate application of the bonding agent to the precise tooth area that needs treatment.

Likewise, it will be appreciated that the present invention provides an apparatus for applying bonding agents to tooth surfaces which may be disinfected and which is disposable, thereby enabling the dentist to maintain an aseptic environment.

In addition, it will be appreciated that the present invention provides apparatus and methods for applying bonding agents to tooth surfaces which permit the bonding agent to be applied directly to the teeth from a sterile source not exposed to air, light, and airborne contaminants. As a result, the present invention does not require the use of a transfer pad.

It will also be appreciated that the present invention provides apparatus and methods of applying bonding agents to tooth surfaces which give the dentist greater control over the flow of bonding agent to the tooth surface. In this way, a proper amount of bonding agent is applied to the tooth surface, not an excessive or insufficient amount.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for controlled application of a dental agent to a predetermined tooth surface, comprising:

reservoir means for holding a quantity of dental agent, said reservoir means being constructed of a chemically inert material with respect to the dental agent and said reservoir means being sufficiently opaque to prevent light-initiated activation of the dental agent;

means for applying the dental agent to a desired location on the tooth surface, the proximal end of the applying means being in communication with the reservoir means such that the dental agent is applied under hydraulic pressure by the distal end of the applying means, said applying means being generally tubular in shape and curved to facilitate application of the dental agent to the tooth surface;

brush means slidably secured within the applying means and comprising a first portion which is slidably adjustable and which extends sufficiently beyond the distal end of the applying means in order to provide for application of the dental agent to the predetermined tooth surface using either a pinpoint-type application to the tooth surface or a fanned out, broad brush type application to the tooth surface, and a second portion which extends into said distal end of the applying means so as to contact said dental agent and so as to permit flow of said dental agent through said brush means; and means for controlled dispensing of the dental bonding agent from the reservoir means to the distal end of the applying means in order to control the flow of the dental agent onto the predetermined tooth surface.

2. An apparatus for applying a dental agent to a tooth surface as defined in claim 1, wherein the applying means is removably attached to the reservoir means.

3. An apparatus for applying a dental agent to a tooth surface as defined in claim 1, wherein the reservoir means comprises a syringe barrel and the controlled dispensing means comprises a plunger located within the syringe barrel for controlling the flow of the dental agent.

4. An apparatus for applying a dental agent to a tooth surface as defined in claim 1, wherein the brush means comprises a plurality of bristles secured within the distal end of the applying means, said bristles extending a distance from the distal end of the applying means in the range from about 1/16 inch to about 5/16 inch.

5. An apparatus for applying a dental agent to a tooth surface as defined in claim 1, wherein the brush means comprises a plurality of bristles secured within the distal end of the applying means, the distance said bristles extend from the distal end of the applying means being adjustable.

6. An apparatus for applying a dental agent to a tooth surface as defined in claim 1, wherein the bristles are constructed of soft nylon having a diameter in the range from about 0.002 inches to about 0.005 inches.

7. An apparatus for applying a dental agent to a tooth surface as defined in claim 1, wherein the dental agent comprises a dental sealant.

8. An apparatus for applying a dental agent to a tooth surface as defined in claim 1, wherein the dental agent comprises a pit and fissure sealant.

9. An apparatus for applying a dental agent to a tooth surface as defined in claim 1, wherein the dental agent comprises a dentin sealant.

10. An apparatus for applying a dental agent to a tooth surface as defined in claim 1, wherein the dental agent comprises a dental bonding agent.

11. An apparatus for controlling application of a dental agent to a predetermined tooth surface comprising:

a reservoir for holding a quantity of a dental agent, said reservoir being constructed of a chemically inert material with respect to the dental agent, and said reservoir being sufficiently opaque to prevent light-initiated activation of the dental agent;

a generally tubular-shaped member for applying the dental agent to a tooth surface, the proximal end of said tubular member being removably secured to and in communication with the reservoir such that the dental agent flows through the tubular member from the proximal end of the tubular member to the distal end of the tubular member, said tubular member being curved to facilitate application of the dental agent to the tooth surface;

brush means slidably secured within the distal end of the tubular member so as to substantially fill at least the distal end of the tubular member and so as to contact said dental agent within said distal end of the tubular member, said brush means thereby permitting flow of the dental agent therethrough and the length of said brush means extending beyond the distal end of the tubular member being slidably adjustable in order to provide for application of the dental agent to the predetermined tooth surface using either a pinpoint-type application to the tooth surface or a fanned out, broad brush type application to the tooth surface as desired; and means for controlling dispensing of the dental agent, said dispensing means being capable of controlling the flow rate of the dental agent from the reservoir onto the predetermined tooth surface.

12. An apparatus for applying a dental agent to a tooth surface as defined in claim 11, wherein the tubular member is threadably attached to the reservoir.

13. An apparatus for applying a dental agent to a tooth surface as defined in claim 11, wherein the tubular member is attached to the reservoir with a luer-lock.

14. An apparatus for applying a dental agent to a tooth surface as defined in claim 11, wherein the tubular member is permanently secured to the reservoir.

15. An apparatus for applying a dental agent to a tooth surface as defined in claim 11, wherein the reservoir comprises a syringe barrel and wherein the controlled dispensing means comprises a plunger located within the syringe barrel for controlling the flow of the dental agent.

16. An apparatus for applying a dental agent to a tooth surface as defined in claim 15, wherein the brush means comprises a plurality of bristles secured within the distal end of the tubular member, said bristles extending a distance from the distal end of the tubular member in the range from about 1/16 inch to about 5/16 inch.

17. An apparatus for applying a dental agent to a tooth surface as defined in claim 16, wherein the bristles are constructed of soft nylon having a diameter in the range from about 0.002 inches to about 0.005 inches.

18. An apparatus for applying a dental agent to a tooth surface as defined in claim 11, wherein the dental agent comprises a dental sealant.

19. An apparatus for applying a dental agent to a tooth surface as defined in claim 11, wherein the dental agent comprises a pit and fissure sealant.

20. An apparatus for applying a dental agent to a tooth surface as defined in claim 11, wherein the dental agent comprises a dentin sealant.

21. An apparatus for applying a dental agent to a tooth surface as defined in claim 11, wherein the dental agent comprises a dental bonding agent.

22. An apparatus for controlling application of a dental agent to a predetermined tooth surface comprising:
   a reservoir for holding a quantity of dental agent, said reservoir being constructed of a chemically inert material with respect to the dental agent, and said reservoir being configured to prevent initiation of reaction with respect to the dental agent prior to application of the predetermined tooth surface;
   a generally tubular-shaped member for applying the dental agent to a tooth surface, the proximal end of said tubular member being in communication with the reservoir such that the dental agent flows through the tubular member from the proximal end of the tubular member to the distal end of the tubular member, said tubular member being curved to facilitate application of the dental agent to the tooth surface;
   a brush, comprising a plurality of bristles secured within the distal end of the tubular member so as to substantially fill at least the distal end of the interior of the tubular member and so as to contact the dental agent within said distal end, said brush thereby permitting flow of the dental agent therethrough, at least a portion of said brush extending sufficiently beyond the distal end of the tubular member in order to provide for application of the dental agent to the predetermined tooth surface and wherein the length of the brush extending beyond the distal end of the tubular member is slidably adjustable in order to provide for application of the dental agent to the predetermined tooth surface using either a pinpoint-type application to the tooth surface of a fanned out, broad brush type application to the tooth surface as desired; and
   means for controlling dispensing the dental agent, said dispensing means being capable of controlling the flow rate of the dental agent from the reservoir onto the predetermined tooth surface.

23. An apparatus for applying a dental agent to a tooth surface as defined in claim 22, wherein the plurality of bristles are packed within the distal end of the tubular member such that friction between the bristles and the tubular member secures the bristles in place.

24. An apparatus for applying a dental agent to a tooth surface as defined in claim 22, wherein the bristles are constructed of soft nylon having a diameter in the range from about 0.002 inches to about 0.005 inches.

25. An apparatus for applying a dental agent to a tooth surface as defined in claim 22, wherein the tubular member is removably attached to the reservoir.

26. An apparatus for applying a dental agent to a tooth surface as defined in claim 25, wherein the tubular member is attached to the reservoir with a luer-lock.

27. An applicator tip for controlled application of a dental agent to a predetermined tooth surface, comprising:
   a generally tubular-shaped member for applying dental agent to a tooth surface, the proximal end of said tubular member being configured to be removably attached to a syringe barrel holding a quantity of dental agent, said tubular member being curved to facilitate precise application of the dental agent to the predetermined tooth surface, and said tubular member being constructed of a chemically inert material with respect to the dental agent, and said tubular member being configured to prevent initiation of reaction with respect to the dental agent prior to application on the predetermined tooth surface; and
   a brush, comprising a plurality of bristles slidably secured within the distal end of the tubular member, said brush permitting flow of the dental agent through said bristles, and the length of said brush extending beyond the distal end of the tubular member being slidably adjustable in order to provide for application of the dental agent to the predetermined tooth surface using either a pinpoint-type application to the tooth surface or a fanned out, broad brush type application of dental agent to the tooth surface as desired.

28. An apparatus for controlled application of a dental bonding agent to a tooth surface, comprising:
   a hollow barrel comprising a reservoir for holding a quantity of dental bonding agent, said barrel being constructed of a chemically inert material with respect to the dental bonding agent, and said reservoir being sufficiently opaque to prevent light-initiated activation of the bonding agent;
   a generally tubular shaped member for applying dental bonding agent to a tooth surface, the proximal end of said tubular member being removably secured to and in communication with the reservoir such that the dental bonding agent flows through the tubular member from the proximal end of the tubular member to the distal end of the tubular member, said tubular member being curved to facilitate precise application of the bonding agent to the predetermined tooth surface;
   a brush, comprising a plurality of bristles secured within the distal end of the tubular member so as to contact the bonding agent therein, said brush permitting flow of the dental bonding agent through said bristles, at least a portion of said brush extending sufficiently beyond the distal end of the tubular member in order to provide for application of the dental bonding agent to the predetermined tooth surface and wherein the length of the brush extending beyond the distal end of the tubular member is slidably adjustable in order to provide for application of the dental agent to the predetermined tooth surface using either a pinpoint-type application to the tooth surface of a fanned out, broad brush type application to the tooth surface as desired; and
   a plunger having a plunger head longitudinally movable within the barrel, said plunger controlling the flow rate of the bonding agent from the barrel and onto the predetermined tooth surface.

29. An apparatus for applying a dental bonding agent to a tooth surface as defined in claim 28, wherein the plurality of bristles are packed within the distal end of the tubular member such that friction between the bristles and the tubular member secures the bristles in place.

30. An apparatus for applying a dental bonding agent to a tooth surface as defined in claim 28, wherein the bristles are constructed of soft nylon having a diameter in the range from about 0.002 inches to about 0.005 inches.

* * * * *

UNITED STATES PATENT AND TRADEMARK OFFICE
CERTIFICATE OF CORRECTION

PATENT NO. : 4,997,371

DATED : March 5, 1991

INVENTOR(S) : Dan E. Fischer

It is certified that error appears in the above-identified patent and that said Letters Patent is hereby corrected as shown below:

Title page, column 1, line 3, where Assignee is listed, "Honda Giken Kogyo Kabushiki Kaisha, Tokyo, Japan" should be --Ultradent Products, Inc., Salt Lake City, Utah--

Title page, column 2, line 20, "Lyon & Lyon" should be --Workman, Nydegger & Jensen--

Column 2, line 16, "is exposes" should be --it exposes--

Signed and Sealed this

Twenty-third Day of February, 1993

Attest:

STEPHEN G. KUNIN

*Attesting Officer*     *Acting Commissioner of Patents and Trademarks*